US011626001B1

(12) United States Patent
Khmelev et al.

(10) Patent No.: US 11,626,001 B1
(45) Date of Patent: Apr. 11, 2023

(54) WEARABLE SYSTEM FOR DETECTION OF ENVIRONMENTAL HAZARDS

(71) Applicant: UIPCO, LLC, San Antonio, TX (US)

(72) Inventors: Yevgeniy Viatcheslavovich Khmelev, San Antonio, TX (US); Christopher Russell, The Colony, TX (US); Gregory David Hansen, San Antonio, TX (US); Nathan Lee Post, Rockport, TX (US); Ashley Raine Philbrick, San Antonio, TX (US); Nolan Serrao, Plano, TX (US); Ruthie D. Lyle, Durham, NC (US); Pooja Krishnaswamy, McKinney, TX (US); Noemy Diosdado, Como, TX (US)

(73) Assignee: United Services Automobile Association (USAA), San Antonio, TX (US)

(*) Notice: Subject to any disclaimer, the term of this patent is extended or adjusted under 35 U.S.C. 154(b) by 0 days.

(21) Appl. No.: 17/387,550

(22) Filed: Jul. 28, 2021

Related U.S. Application Data

(60) Provisional application No. 63/057,773, filed on Jul. 28, 2020.

(51) Int. Cl.
| | |
|---|---|
| *G08B 21/10* | (2006.01) |
| *G01S 19/42* | (2010.01) |
| *G01D 21/02* | (2006.01) |
| *H04L 67/12* | (2022.01) |

(52) U.S. Cl.
CPC ............ *G08B 21/10* (2013.01); *G01D 21/02* (2013.01); *G01S 19/42* (2013.01); *H04L 67/12* (2013.01)

(58) Field of Classification Search
CPC ........ G08B 21/10; G01D 21/02; G01S 19/42; H04L 67/12
See application file for complete search history.

(56) References Cited

U.S. PATENT DOCUMENTS

| | | | | |
|---|---|---|---|---|
| 6,671,226 B1 * | 12/2003 | Finkel | .................... | A61H 3/068 |
| | | | | 367/116 |
| 8,494,507 B1 * | 7/2013 | Tedesco | ................. | G09B 21/00 |
| | | | | 455/418 |
| 9,576,460 B2 * | 2/2017 | Dayal | .................... | G08B 21/02 |
| (Continued) | | | | |

FOREIGN PATENT DOCUMENTS

| | | | |
|---|---|---|---|
| CN | 104127302 A | * | 11/2014 |
| RU | 168009 U1 | * | 1/2017 |

*Primary Examiner* — Joseph H Feild
*Assistant Examiner* — Rufus C Point
(74) *Attorney, Agent, or Firm* — Plumsea Law Group, LLC

(57) ABSTRACT

The disclosed wearable device systems include several features for alerting and guiding persons who are approaching or near to potentially hazardous or high-risk conditions in their nearby environment. Sensor data from wearable devices (also referred to herein as "wearables") are used to determine the presence of various unsafe environmental conditions and phenomenon, including dangerous terrain or other unusual conditions. The wearable would be used to warn a person, for example via auditory or haptic-based feedback, if the person is about to encounter an unsafe condition. In particular, the proposed systems can be of great benefit to the visually impaired, those persons with physical disabilities, or persons otherwise vulnerable to particular environmental conditions.

20 Claims, 9 Drawing Sheets

(56) References Cited

U.S. PATENT DOCUMENTS

| | | | |
|---|---|---|---|
| 10,251,788 B1* | 4/2019 | Phan | A61F 9/08 |
| 2005/0273809 A1* | 12/2005 | Kendall | H04N 21/47 |
| | | | 348/E7.024 |
| 2006/0129308 A1* | 6/2006 | Kates | A61H 3/061 |
| | | | 701/532 |
| 2007/0080801 A1* | 4/2007 | Weismiller | G01S 5/0226 |
| | | | 340/539.13 |
| 2011/0200214 A1* | 8/2011 | Knox | H04R 25/50 |
| | | | 381/314 |
| 2011/0249839 A1* | 10/2011 | Mindlin | H04R 25/43 |
| | | | 381/314 |
| 2013/0274040 A1* | 10/2013 | Coza | A63B 43/004 |
| | | | 473/570 |
| 2015/0196101 A1* | 7/2015 | Dayal | A61H 3/061 |
| | | | 63/1.11 |
| 2015/0324698 A1* | 11/2015 | Karaoguz | H04L 67/12 |
| | | | 706/46 |
| 2016/0063893 A1* | 3/2016 | Kanuganti | H04N 21/8545 |
| | | | 348/62 |
| 2016/0078278 A1* | 3/2016 | Moore | G02B 27/017 |
| | | | 345/8 |
| 2016/0080897 A1* | 3/2016 | Moore | G01S 19/49 |
| | | | 340/539.13 |
| 2016/0093207 A1* | 3/2016 | Di Censo | G08G 1/005 |
| | | | 340/944 |
| 2016/0127698 A1* | 5/2016 | Mali | G01S 15/04 |
| | | | 348/62 |
| 2017/0189751 A1* | 7/2017 | Knickerbocker | A61B 5/1114 |
| 2019/0018551 A1* | 1/2019 | Shintani | H04N 21/4312 |
| 2019/0278236 A1* | 9/2019 | Koshy | G05B 23/0259 |
| 2020/0043368 A1* | 2/2020 | Brathwaite | G08B 6/00 |
| 2020/0064141 A1* | 2/2020 | Bell | G09B 21/003 |
| 2020/0286289 A1* | 9/2020 | Mitchell | H04W 4/029 |

* cited by examiner

WEARABLE SYSTEM FOR DETECTION OF ENVIRONMENTAL HAZARDS

CROSS-REFERENCE TO RELATED APPLICATION

This application claims the benefit of U.S. Provisional Patent Application Ser. No. 63/057,773 filed on Jul. 28, 2020 and titled "Wearable System for Detection of Environmental Hazards", the disclosure of which is incorporated by reference in its entirety.

TECHNICAL FIELD

The present disclosure generally relates to a system for detecting unsafe conditions and, more particularly, to a system that utilizes data collected by one or more wearable devices to detect dangerous conditions and alert and/or guide users of such conditions.

BACKGROUND

Vehicles or persons travelling on foot may encounter hazardous conditions such as flood waters, ice, or oil on a roadway or path. For example, according to FEMA, just six inches of fast-moving water could knock down an adult pedestrian. For an individual traveling on foot, water measuring about 20" deep and moving with a velocity of two miles per hour will present an increased risk to most adults. Ice and oil slicks may cause pedestrians to lose their balance, and may often result in dangerous accidents. In addition, just 12 inches of fast-moving flood water could cause an average vehicle to lose firm contact with the roadway, rendering steering and braking systems ineffective.

These and other dangerous environmental conditions, stemming from weather, uneven ground surfaces, construction, and other sources, can be dangerous to individuals, particularly in cases where there is low visibility. Individuals may approach dangerous conditions and reach a very close proximity to the individuals before the individual becomes aware of the danger. For example, some snowstorms or thunderstorms develop very quickly and/or may travel rapidly across the countryside. Heavy storms may cause flooding or road blocks, which can pose a danger to pedestrians and drivers alike. Similarly, cracks in sidewalks and roads, as well as unexpected debris, are associated with a greater likelihood of accidents and injury. Individuals may benefit from early notice and guidance as to how to avoid these hazards.

There is a need in the art for systems and methods that address the shortcomings discussed above. In particular, there is a need in the art for monitoring systems that can provide personalized, real-time guidance to a user.

SUMMARY

In one aspect, a wearable environmental monitoring system includes an article of apparel including a first sensor and a second sensor, and a system controller associated with the article of apparel that further includes a processor and machine-readable media including instructions. The instructions, when executed by the processor, cause the processor to receive first data about one or more conditions of a physical environment in a sensor range of the article of apparel from the first sensor, and to determine, based on the first data, that an unsafe condition is present at a first location in the physical environment. In addition, the instructions cause the processor to receive second data about a speed and direction of the article of apparel during a first time period from the second sensor, and to determine, based on the second data, that the article of apparel was approaching the first location during the first time period. Furthermore, the instructions cause the processor to cause, in response to the determination that the article of apparel is approaching the first location during the first time period, a first alert to be generated by a first feedback component of the article of apparel.

In another aspect, a wearable environmental monitoring system for detecting unsafe conditions includes a first article of apparel to which a first sensor and a first feedback component are attached, a system controller associated with the first article of apparel and connected to both the first sensor and the first feedback component, and a rechargeable battery configured to provide power to the wearable environmental monitoring system.

In another aspect, a method of alerting a user of a wearable environmental monitoring system to the presence of a nearby unsafe condition includes a first step of receiving first data from a first sensor about one or more conditions of a physical environment in a sensor range of an article of apparel worn by the user, where the article of apparel includes the first sensor. A second step includes determining, based on the first data, that an unsafe condition is present at a first location in the physical environment, and a third step includes receiving second data about a speed and direction of the user during a first time period from a second sensor of the article of apparel. In addition, a fourth step includes determining, based on the second data, that the user was approaching the first location during the first time period. Furthermore, a fifth step includes causing, in response to the determination that the user is approaching the first location during the first time period, a first alert to be generated by a first feedback component of the article of apparel.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF EMBODIMENTS

Figure 1:
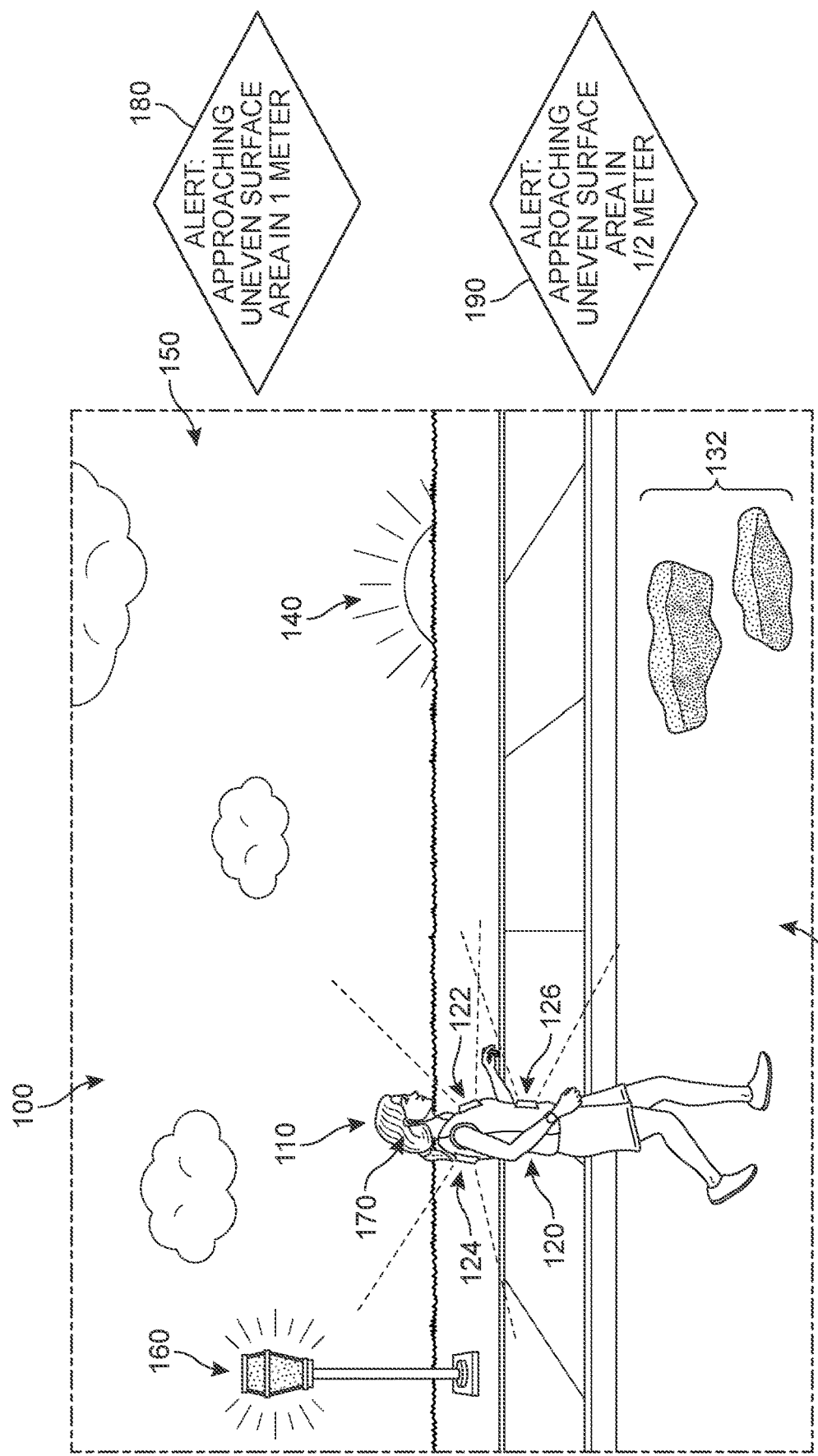
FIG. 1 is an illustration depicting an overview of a wearable environmental monitoring system.

The disclosed wearable device systems include several features for alerting and guiding persons who are approaching or near to potentially hazardous or high-risk environmental conditions. In one example, the disclosed systems are configured to receive sensor data from wearable devices (also referred to herein as "wearables"), such as smart devices embedded in articles of apparel, to detect the presence of various environmental conditions, including dangerous terrain or other unusual conditions. It will be understood that, for purposes of this specification and claims, the term "environmental condition" shall refer to conditions in the general proximity of an individual person. Environmental conditions may include indoor and/or outdoor conditions; furthermore, dangerous or hazardous environmental conditions may include unsafe conditions as determined by the wearer's physical abilities and means of transport.

The proposed systems and methods contemplate an arrangement in which one or more wearables including such sensors would be used to warn a person if they are about to encounter an unsafe condition. For example, as will be described in detail herein, a wearable with one or more sensors could scan the ground near a user and detect icy walkway conditions or an uneven sidewalk. In some embodiments, the system can connect to a network to share information about the location or status of safety hazards. The wearable system could then generate an audio and/or haptic-based alert to the person to warn them that they are, for example, about to step on ice or pass over an uneven part of the sidewalk. In particular, the proposed systems can be of great benefit to the visually impaired, those persons with physical disabilities, or persons otherwise vulnerable to particular environmental conditions.

The embodiments disclosed herein assist the user in detecting unsafe conditions, such as surface irregularities on the road and other paths, slippery surfaces, obstacles, and other aspects which may create dangerous conditions while traveling on a road or path. As one non-limiting example, it can be appreciated that driving, biking, or walking on ice can be extremely dangerous. Ice often causes vehicles to lose traction, resulting in skidding and rendering steering and braking systems ineffective. Black ice is particularly dangerous because it remains difficult to detect. For pedestrians, undetected black ice can result in dangerous slips and falls resulting in serious injury. Similarly, oil slicks and other hazards such as fallen trees, boulders, broken-down vehicles, fallen power lines, broken or uneven surfaces, and other objects in a roadway can create serious hazards for drivers. As used herein, the term "pedestrian" shall include a walker, a jogger, a runner, or a hiker, as well as any person engaging in other similar activities. The term "rider" or "driver" refers to users of vehicles such as cars and trucks, as well as persons using bicycles, hoverboards, skateboards, wheelchairs, scooters, Segways®, and other personal transporter vehicles. The embodiments described herein detect a broad range of irregularities in roadways or paths using smart sensors, which may be embedded or otherwise disposed within a user's article of apparel (i.e., in clothing or footwear or other wearable accessories). For example, the sensor(s) analyze the images for particular environmental conditions, determine the boundaries and type of hazard, and alert the user of potential danger.

Furthermore, for purposes of this disclosure, the term "article of apparel" refers to any garment, footwear, or accessory configured to be worn on or carried by a human. Some non-limiting examples of articles of apparel include tops, bottoms, outerwear, helmets, hats, caps, shirts, jackets, coats, vests, undershirts, tank tops, pants, leggings, gloves, scarves, armbands, headbands, jewelry, hair clips, belts, waist bands, belt bags ("fanny packs"), shorts, sleeves, knee pads, elbow pads, socks, shoes, boots, backpacks, duffel bags, cinch sacks, and straps, as well as numerous other products configured to be worn on or carried by a person. In some cases, the article of apparel can also be worn by an animal or disposed on another article carried by or in possession of the user.

For purposes of clarity, an overview of one embodiment of the proposed systems and methods is illustrated with reference to FIG. 1. FIG. 1 is an illustration of a wearable environmental monitoring and alert system ("system") 100. As shown in FIG. 1, system 100 may include a smart article 120 (shown here as an article of clothing comprising a "top" in which a plurality of sensors has been embedded or otherwise attached) worn by a first user 110. In this case, the top is a vest that can be worn alone or over another shirt, dress, or other top. The smart article 120 in this case includes a first (forward-facing) sensor 122 located on a torso region of the top, and a second (rearward-facing) sensor 124 located on a back region of the top. As will be discussed herein, in other embodiments, there may be fewer or more sensors, and the sensors can be disposed at other or additional locations on the smart article 120.

In FIG. 1, first user 110 is a jogger moving through a neighborhood park 150 near dusk, as symbolized by setting sun 140. While the park 150 may or may not include artificial lights 160, such light sources can be far apart or limited in number, and offer little illumination for navigating unexpected unsafe conditions found along a pedestrian path 130 in the park 150. For example, a first unsafe condition ("first condition") 132 comprising a set of potholes is depicted only a few feet in front of the first user 110, who approaches in dim lighting and at speed. In this case, the first sensor 122, which in some embodiments may include night vision cameras implementing techniques as image intensification, active illumination, and thermal imaging to capture information in low-light conditions, can detect the approaching first condition 132 and, in response, the system can cause a signal to be generated to alert the user and/or re-route the first user 110. In one embodiment, there may be only one alert, or the alert may repeat until the danger has passed, depending on the user's preferences and system configuration. The repeating alerts may be static (i.e., unchanging) or vary as the user comes closer to the detected condition. As one non-limiting example, two alerts are presented to first user 110 in FIG. 1. Initially, a first alert 180 ("Alert: Approaching uneven surface area in one meter") is emitted as audio via headphones 170 worn by first user 110. This is followed by a second alert 190 ("Alert: Approaching uneven surface area in half a meter") that is emitted as audio through headphones 170 as the first user 110 comes closer to the first condition 132.

In different embodiments, such audio output can be personalized and/or selected from a list of available audio types. Various types of sounds can be incorporated into the warning, and volume, speed of playback, and voice type can be adjusted to correspond to the user's preferences. The spoken words can be entered by the user or pre-selected by the system defaults. For example, additional spoken navigation type directions may be produced, such as "Move forward", "Go to your left". In some embodiments, rather than spoken utterances, the audible alert or message can be conveyed by different types of sounds (e.g., shrill whistles, ringing, beeps, chimes, tones, etc.) that can change in type, intensity (e.g., loudness or sound level), and frequency based on the device's proximity to the detected unsafe condition. In other cases, the alert can be presented by proprioceptive or haptic feedback emitted by the wearable article. In one embodiment, smart article 120 can include one or more haptic feedback components that produce various types of vibrations or other touch-based information to the user in order to convey information. As one non-limiting example, the frequency and/or intensity (i.e., strength) of the vibration can increase as proximity to the unsafe condition increases, and decrease as proximity decreases.

The system 100 can further include a system controller module (see FIG. 2) that is integrated or embedded or otherwise connected to the sensors of smart article 120. The controller may include various computing and communications hardware, such as servers, integrated circuits, displays, etc. Further, a controller may include a device processor and a non-transitory computer readable medium including instructions executable by device processor to perform the processes discussed herein. The components of controller may be implemented in association with a mobile device, such as smart phone or tablet, and/or be in communication with a cloud-based control center or conditions monitoring center via a network connection. Thus, in different embodiments, a controller may include networking hardware configured to interface with other nodes of a network, such as a LAN, WLAN, or other networks. In some embodiments, the controller may be configured to receive data from a plurality of sources and communicate information to one or more external destinations. Accordingly, a controller may include a receiver and a transmitter. It will be appreciated that, in some embodiments, the receiver and transmitter may be combined in a transceiver. Any suitable communication platforms and/or protocols may be utilized for communication between the controller and other components of the system. Since the various sources of information may each have their own platform and/or protocol, system 100 may be configured to interface with each platform and/or protocol to receive the data.

In some embodiments, the computer readable medium may include instructions executable by the device processor to perform steps including receiving data from one or more devices or sensors. In some embodiments, computer readable medium may include instructions for receiving data from one or more wearable sensors. For example, the system 100 may also include or communicate with a device that further includes a display configured to display data, which may include messages, information, and/or interactive options for the user to submit requests or responses to the system 100. While in some embodiments the display is provided with system 100, for example, as a panel display embedded on the smart article 120, in other embodiments, the system 100 may be configured to display information on user's own device.

It will also be noted that while the smart article 120 is illustrated as being configured to be worn on the torso of the wearer, in other embodiments, system 100 may include smart wearables worn on other parts of the body. For example, other types of wearable devices may be worn around the neck, arm, or waist; attached to clothing; or worn in any other manner. Additionally, or alternatively, system 100 may include or be in communication with other types of devices besides wearable devices. For example, the controller may be configured to receive data from various Internet of Things (IoT) devices. Exemplary such devices may include various types of environmental sensors, such as temperature sensors, pressure sensors, moisture and humidity sensors, cloud databases, other users' sensors, etc.

Figure 2:
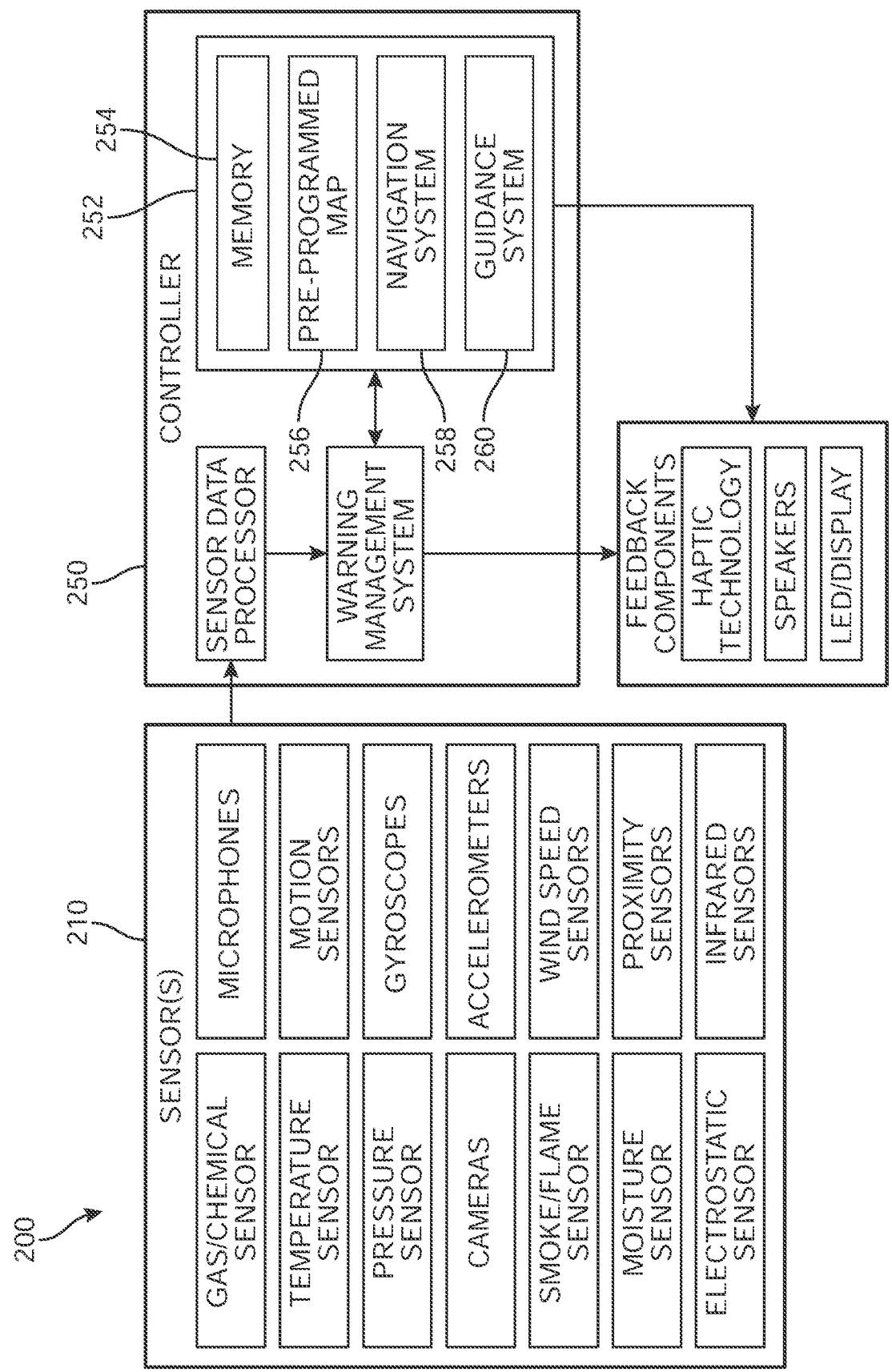
FIG. 2 is a schematic diagram of a wearable environmental monitoring system, according to an embodiment.

In order to provide the reader with a greater appreciation of some of the embodiments, FIG. 2 depicts a schematic overview of an embodiment of a wearable environmental monitoring and alert system ("system") 200. In the embodiment of FIG. 2, the system 200 includes a plurality of sensor devices ("sensors") 210, a controller 250, and signaling components 270. The system 200 further includes a power source (not shown in FIG. 2), such as a rechargeable battery, which may be recharged by the user by a charger cable. In some embodiments, the system 200 includes a solar powered battery, and the smart apparel may include one or more solar cells distributed throughout the external surface of the wearable. Furthermore, while in some embodiments various modules and components of system 200 can be configured to connect to a network (see FIG. 3), it can be appreciated that the system 200 is able to function and provide feedback to a user while offline. In other words, a user can rely on the system 200 as an independent, comprehensive system that is able to work in areas without a network or in situations where the user does not desire any such connection.

In different embodiments, the sensors 210 can include one or more types of a device, module, machine, or subsystem whose purpose is to detect events or changes in its environment and convey the detected information to the sensor data processor 220. The smart wearable apparel selected by a user can include some or all of these sensor devices, and in some cases, there may be multiple instances of the same type of sensor included in the smart wearable apparel and arranged at different locations around the apparel. Some non-limiting examples of such sensors include (a) Smoke, Gas and Alcohol (and/or other chemicals) sensors; (b) Temperature sensors; (c) Pressure sensors; (d) Cameras and other image and/or light sensors; (e) Smoke/Flame sensors; (f) Moisture/Humidity sensors; (g) Electrostatic sensors; (h) Audio sensors and other sound/volume sensors (e.g., microphones); (i) Motion/speed sensors; (j) Gyroscopes; (k) Accelerometers; (l) Wind Speed sensors; (m) Proximity sensors; and (n) Infrared and Heat sensors. In addition, in some embodiments, sensors 210 can include ultrasonic sensors, touch sensors, aerosol characterization sensors, magnetometers, color sensors, tilt sensors, and flow and level sensors. Thus, in different embodiments, sensors 210 may collect data regarding location, speed, and direction of the user wearing the system and/or of objects near the user. Additionally, or alternatively, in some embodiments, the sensors 210 may be configured to collect atmospheric data, such as atmospheric temperature and/or atmospheric pressure. Monitoring such parameters may enable the system to detect dangerous weather conditions, such as storms, etc. In addition, in some embodiments, the sensors 210 may include biometric sensors configured to monitor personal data regarding the wearer of the wearable apparel, for example by collecting data from the wearable's heartrate monitor and/or pedometer, in order to assess the physical condition, level of activity and/or ability of the wearer.

In some cases, sensors 210 can refer to one or more of a stationary internet of things (IoT) device(s) ("smart sensors") that communicate over a network. Smart sensors could comprise any of a variety of different IoT devices and other smart devices that may include one or more sensors. The smart sensors can be located in the apparel itself, or be stationed at other locations in the area (see FIG. 7). Supplemental data from such smart sensors can be received by the system and used to determine routes and areas of danger and/or safety with more precision.

In different embodiments, data collected by sensors 210 can be used by the system 200 to identify potential unsafe environmental conditions and/or present navigational to help guide a person to a safe position. In FIG. 2, data is transmitted to a sensor data processor 220 of controller 250 which prepares the data for use by a warning management system 230 (see FIG. 3). The warning management system 230 can access various modules 252 including but not limited to a memory 254, pre-programmed maps 256, a navigation system 258, a guidance system 260, and/or a communication system 262. As a general matter, pre-programmed maps 256 can refer to downloaded or otherwise offline (locally stored) information about the geographical area and/or terrain the user is traveling in. The maps can be provided with the system 200 or can be downloaded and/or updated via a network as desired or necessary. In some embodiments, the maps can include information for outdoor areas, as well as indoor areas such as large stores, malls, schools, businesses, offices, etc. In one embodiment, a user may upload a map for an indoor location that he or she is familiar with and frequently visits. In one embodiment, the sensors 210 can collect data that will be used to automatically generate maps based on indoor positioning systems, user-uploaded maps, as well as maps obtained from municipal databases showing detailed schematic layouts of various buildings and street layouts. These maps can be used, in conjunction with user feedback and preferences, to identify preferred routes and secondary (alternative) routes.

In some embodiments, this information may be used in conjunction with navigation system 258, which includes a location data processor that can identify a user's current location and heading, for example via a GPS included in the system 200. The guidance system 260 comprises any system capable of providing directions and/or other kinds of routing information between two or more locations. In some cases, guidance system 260 can provide directions in an outdoor environment. In other cases, guidance system 260 can provide directions in an indoor environment. In some cases, guidance system 260 may provide directions in both outdoor and indoor environments.

In different embodiments, output from the warning management system 230 (as will be described in greater detail in FIG. 3) can cause various alerts or other messages to be generated by one or more feedback components 270. For example, feedback components 270 can include haptic technology for tactile-based feedback, speakers or audio jack for auditory-based feedback, and/or a display, LEDs, or video jack for presenting visual indicators and other visual-based information.

In some embodiments, particularly in cases where the feedback components 270 includes or is configured to communicate with an onboard display or user computing device such as a mobile phone or tablet, the system 200 can include interactive options and control mechanisms to the user. For example, a user application ("application" or "app") may be provided by which the user can create an account, select a profile, and/or adjust various settings and preferences. In some embodiments, the application can be downloaded to be accessible locally via the controller 250 or the user's own computing device. The application can in some cases offer a system interface ("interface") for accessing and modifying settings in the system. In some embodiments, the application can be configured to connect a user's device (for example, via a Bluetooth, WiFi, wired, or cellular connection) with an online service provider to add or modify information for the user that may be stored in the cloud, including user settings 262 and the user's desired alert preferences (e.g., SMS messages, audio, visual, haptic, intensity, frequency, etc.) for each device and/or type of unsafe condition. However, even in cases without a display, the user may be able to interact with and control operations of the system. For example, the controller can include mechanical buttons or other mechanisms by which the user can adjust various system settings and/or power the system on or off.

In different embodiments, the application can be configured to offer content via native controls presented via an interface. Throughout this application, an "interface" may be understood to refer to a mechanism for communicating content through a client application to an application user. In some examples, interfaces may include pop-up windows that may be presented to a user via native application user interfaces (UIs), controls, actuatable interfaces, interactive buttons or other objects that may be shown to a user through native application UIs, as well as mechanisms that are native to a particular application for presenting associated content with those native controls. In addition, the terms "actuation" or "actuation event" refers to an event (or specific sequence of events) associated with a particular input or use of an application via an interface, which can trigger a change in the display of the application. This can include selections or other user interactions with the application, such as a selection of an option offered via a native control, or a 'click', toggle, voice command, or other input actions (such as a mouse left-button or right-button click, a touchscreen tap, a selection of data, or other input types). Furthermore, a "native control" refers to a mechanism for communicating content through a client application to an application user. For example, native controls may include actuatable or selectable options or "buttons" that may be presented to a user via native application UIs, touch-screen access points, menus items, or other objects that may be shown to a user through native application UIs, segments of a larger interface, as well as mechanisms that are native to a particular application for presenting associated content with those native controls. The term "asset" refers to content that may be presented in association with a native control in a native application. As some non-limiting examples, an asset may include text in an actuatable pop-up window, audio associated with the interactive click of a button or other native application object, video associated with a teaching user interface, or other such information presentation. In some embodiments, the application can also offer users access to a status monitor dashboard that may be used to track and view past alerts, messages, and updates regarding hazardous conditions nearby and potential areas to avoid.

Figure 3:
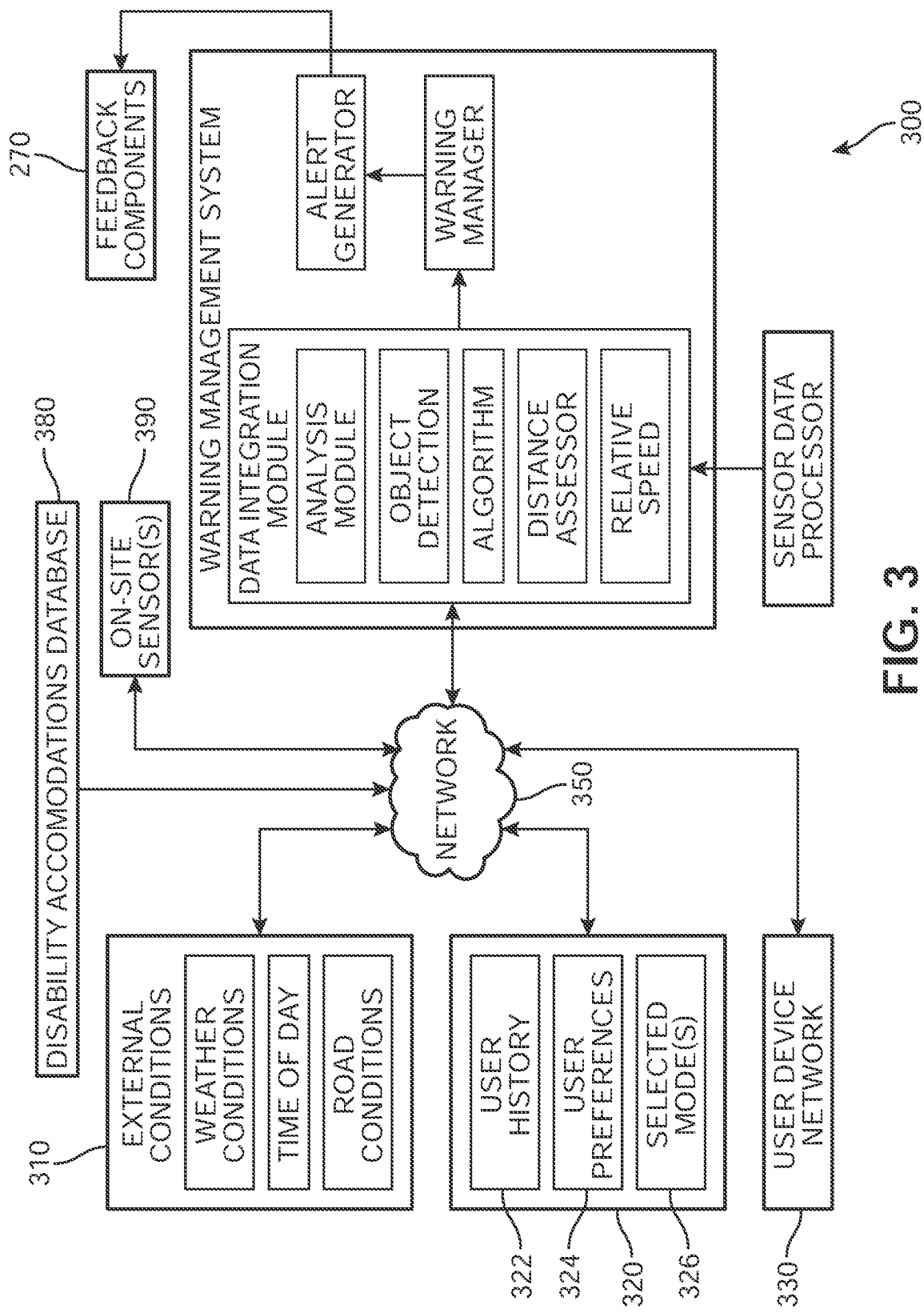
FIG. 3 is a schematic diagram showing some examples of information sources that may be accessed by a warning management system for the wearable environmental monitoring system of FIG. 2, according to an embodiment.

Thus, based at least in part on the data collected by the one or more sensors 210, the controller 250 may be configured to generate and present instructions via feedback components 270 to the user to help avoid danger related to the detected conditions. Referring now to FIG. 3, additional details regarding an embodiment of the warning management system 230 and optional external knowledge sources (e.g., accessed via a network) are illustrated schematically as an information flow process diagram 300. As shown in FIG. 3, the warning management system 230 may communicate with one or more remote systems over a network 350, where network 350 could comprise any wide area network, local area network or other suitable network. In different embodiments, network 350 could include one or more Wide Area Networks (WANs), Wi-Fi networks, Bluetooth or other Personal Area Networks, cellular networks, as well as other kinds of networks. It may be appreciated that different modules could communicate using different networks and/or communication protocols. The modules can include computing or smart devices as well as simpler IoT devices configured with a communications module. The communication module may include a wireless connection using Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. In many cases, the communication module is a wireless connection; however, wired connections may also be used. For example, the communication module may include a wired serial bus such as a universal serial bus or a parallel bus, among other connections.

In some cases, communication module for warning management system 230 enables warning management system 230 to communicate over network 350, for example, with one or more external database systems. Each external database system can include a server (including processors and memory) and a database. As will be described below, these external database systems may store various kinds of information, including, but not limited to: navigation information, geospatial information, road conditions (for example, real-time traffic patterns), weather information (including, for example, rain, snow, ice and/or flooding forecasts), as well as other kinds of information. It may be appreciated that warning management system 230 may both send and receive information to and from these remote databases. Moreover, it may also be appreciated that in other embodiments, one or more of these databases (or parts of the databases) could be locally disposed within the system.

For purposes of illustration, some non-limiting examples of external databases are depicted in FIG. 3, and include external conditions database 310, a user database 320, a device network 330, and a disability accommodations database 370. The external conditions database 310 may monitor and maintain information regarding current external conditions in the area. Such conditions may include, but are not limited to road and other path conditions, including construction reports, weather conditions, and/or time of day/year and expected illumination levels. Road conditions may include information about the condition of the current road and/or adjacent roadways, as well as sidewalks and recreational paths. These conditions may include current traffic (vehicular and pedestrian) patterns, physical conditions (e.g., potholes), the type of roadway (for example, a neighborhood street, a highway, brick, paved, gravel, grass, sand, etc.), the presence of a stop sign, the presence of a stoplight, the presence of a one-way sign, the presence of traffic cones or other barriers, the number of lanes, as well as possibly other roadway and pathway condition information. Weather conditions could include, for instance, whether it is dry, raining, windy, snowing, and/or if the roads and paths are wet, dry or icy. Time of day can include an explicit time (for example, 3 pm), or a general timeframe such as morning, afternoon, evening and/or late-night. Time of day may also explicitly or implicitly include information about lighting conditions. For example, if the time of day is 9 pm, the system can infer that it is dark outside based on geographic and seasonal information.

In some embodiments, the warning management system 230 may also communicate with, for example, user database 320. The user database 320 may store various information related to the user's activities, settings, and preferences 324, historical information (e.g., regular jogging or driving routes) 322, as well as the user's selected operating mode(s) 326 for the system (see FIG. 4).

Furthermore, in different embodiments, the warning management system 230 can access information from user device network 330. The user device network 330 can comprise one or more wearable environmental monitoring and alert systems ("devices") for multiple users connected over one or more networks 212 to a cloud-based platform ("platform") that is configured to collect, process, and analyze the 'crowd-shared' data. Each device of user device network 330 can include provisions for communicating with, and processing information from the platform as well as other devices in user device network 330. Thus, each device may include one or more processors and memory. Memory may comprise a non-transitory computer readable medium. Instructions stored within memory may be executed by the one or more processors. In addition, each device may include a communication system such as a radio or other provisions for communicating using one or more communication methods. In particular, communication system includes provisions for communicating with other nearby devices and/or platform over network 350. For example, each communication system could include a Wi-Fi radio, a Bluetooth radio, and/or a cellular network radio.

As noted earlier, the environmental monitoring and alert system can be configured to identify location data from each registered device. This location information can be shared with user device network 330, which can track the current location of each device in real-time or near-real-time. In some embodiments, the system may be configured to collect data from multiple wearable devices in order to more accurately detect environmental conditions. Data from multiple devices may be used to determine patterns and/or to triangulate the location of an environmental condition. In such cases, the system may be configured to send instructions to any of the devices from which data is collected. Further, the system may be configured to send instructions to devices other than those from which data is used to detect an environmental condition. Accordingly, the system can detect whether the individual wearers are running, driving, or otherwise moving, in a common direction. If multiple wearers are moving in a common direction, it may be determined that they are moving away from something, such as a dangerous condition. If multiple wearers have been avoiding a common path or making a detour around a particular location, it may be determined that an unsafe condition is present. Similarly, when an individual device determines that the wearer is approaching an unsafe condition, it can share this information with the platform via the user device network 330. The collected information is used to reroute or otherwise alert other users in the area who may be further away but are heading towards the same general area.

Other data may also be interpreted to detect unsafe conditions. For example, in some embodiments, personal data about the wearer may be collected by the wearable devices and considered when determining the existence of dangerous conditions. For example, in some embodiments, the wearable devices may have sensors, such as heartrate monitors and pedometers. If an increase in heartrate and/or pedometer readings is detected, it may be a sign that wearers are fleeing some kind of dangerous condition, or preparing to do so. When considered in conjunction with the aforementioned location, speed, and direction data, a more accurate determination may be made that a dangerous condition is present, especially when data is considered from multiple wearable devices. With multiple devices, not only may the precise location of a dangerous condition be triangulated, but also the accuracy of the determination may be higher.

In addition, in different embodiments, the warning management system 230 can access information from disability accommodations database 380. The disability accommodations database 380 refers generally to one or more databases and repositories in which wheelchair and other disability accessible maps and guidance are maintained stored. This can include both user generated maps and updates, as well as other sources such as WheelMap, AXSmap, GoogleMaps, and other ADA-approved or friendly wayfinding services. Based on the needs and preferences of the user (see selected modes 326) the warning management system 230 can determine if the user is headed towards an area that is difficult to maneuver, and generate alerts and re-routing suggestions. This process will be discussed further with respect to FIG. 8.

Thus, in different embodiments, data from a wide variety of sources can be accessed by the warning management system 230, in addition to the data collected by sensors carried by the smart apparel and processed by sensor data processor 220. The warning management system 230 may rely on this data to detect and identify imminent or approaching environmental hazards. For example, warning management system 230 can apply an object detection algorithm to images (collected by cameras) of the environment around the wearer to determine whether there are potential imminent hazards. In some embodiments, identification of a potential hazard in the roadway can cause the system to re-direct the focus of one or more of the cameras towards that potential hazard for more intensive analysis.

In one embodiment, if analysis of images for a roadway (or other pathway) shows that there is water in the roadway, a call can be made by an analysis module of a data integration module 340 to external conditions database 310 to review local topographic conditions. in another embodiment, the analysis module can trigger a link to external devices such as user device network 330 and on-site sensors 390 (e.g., roadway cameras). In some embodiments, user history 322 contains topographical data collected from previous activity sessions for the wearable for routes that the user takes regularly. Such data may be more detailed and more up-to-date than the information stored in other databases. In some cases, data integration module 340 can refer to stored images obtained by local cameras if the smart apparel's GPS coordinates indicate that it is on a route that the user takes often. In this embodiment, if the GPS coordinates indicate that user history 322 contains information about the current road and the analysis module indicates there is some potential hazard on the roadway, then the user history 322 may return such information to the analysis module. For example, analysis module may compare current images of the roadway immediately in front of the person with images made of the same roadway under hazard-free conditions. In some embodiments, the warning management system can ask the wearer if images taken of the roadway on a particular route are suitable for storage as occurring under hazard-free conditions. In some embodiments, such images may be categorized according to, for example, sunlight, nighttime, time of day, rain or other precipitation or other contextual conditions so that current roadway images may be matched with images taken under similar contextual conditions. Thus, in some embodiments, user history 322 corrects and improves the precision and accuracy of local topographical maps.

In different embodiments, images and other data collected by the sensors are then analyzed for potential hazards. In some embodiments, these potential hazards may include floods, ice, black ice, and oil slicks, as well as other potential hazards, such as uneven pavements, ditches, and other unsafe conditions. If a potential hazard is present ("target hazard") an attempt to determine what it is and/or the type of hazard occurs via an object detection algorithm. A distance assessment engine can determine the estimated distance remaining between the user and the target hazard in real-time. Furthermore, a relative speed module can determine how quickly the user and the target hazard are approaching and the estimated time remaining before the user will be directly adjacent to the target hazard.

In some embodiments, the data gathered from these sources could be fed into a machine learning algorithm. The machine learning algorithm could be used to facilitate learning patterns in external conditions that represent danger to a particular user. Examples of machine learning algorithms that could be used include, but are not limited to: supervised learning algorithms, unsupervised learning algorithms, and reinforcement learning algorithms. In one embodiment, if the data integration module 340 determines there is an imminent hazard in the roadway, it can access a warning manager 360 (see FIG. 4A) to determine what type of feedback(s) to provide to the user. A signal is then transmitted from an alert generator 370 to cause alert(s) to be generated by the one or more feedback components 270 (see FIG. 2).

For example, once the presence and progression of a dangerous condition is determined by the system, messages may be delivered to the feedback component(s) with instructions related to the condition, such as directions for evading, or otherwise avoiding, the dangerous condition. In some cases, the wearer may be proximate to the dangerous condition, but not in its path. Accordingly, the system may send a message to the user informing them that there is a hazard nearby, but that they are in a safe location and do not need to adjust their heading. Conversely, if the wearer is in the path of the unsafe condition, the system may present messages instructing the wearer to take an alternate route that enables them to avoid the hazard.

Figure 4A:
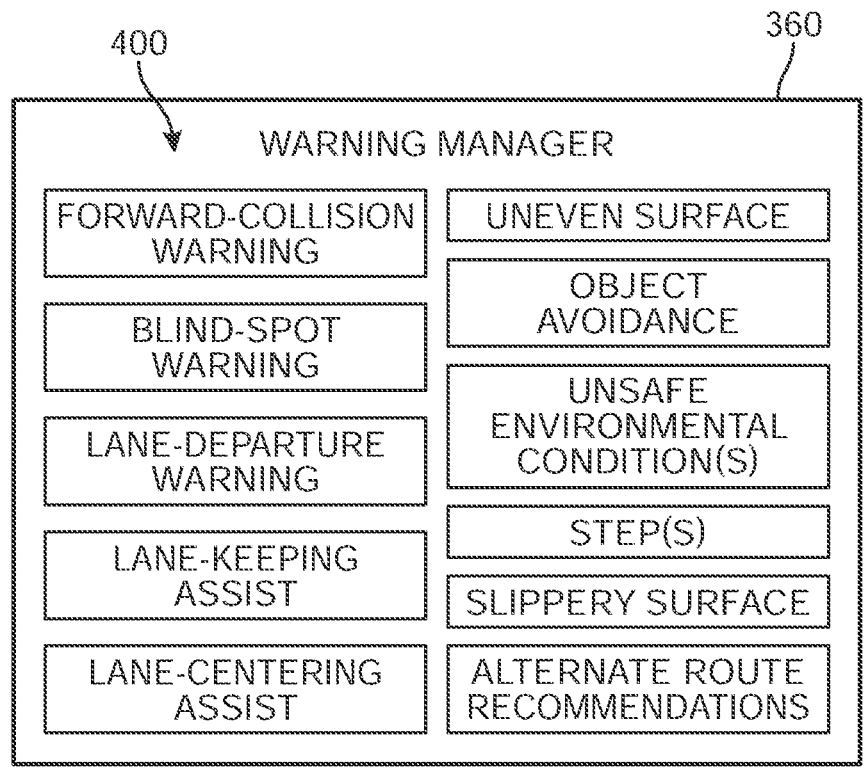
FIG. 4A is a schematic diagram of some safety response mechanisms for use by a warning manager, according to an embodiment.
Figure 4B:
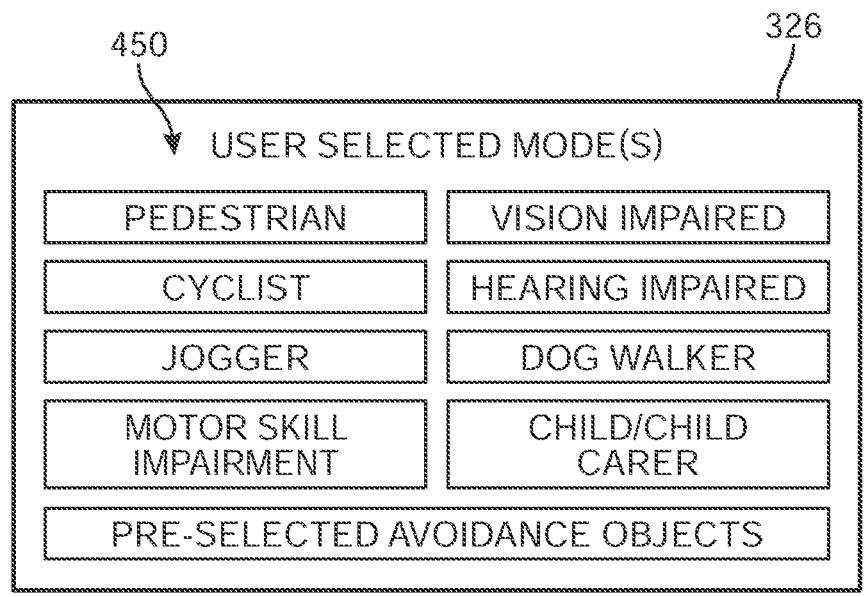
FIG. 4B is a schematic diagram of some profile options that may be implemented by the system, according to an embodiment.

Additional details regarding the warning manager 360 are now provided with respect to FIG. 4A. As noted above, the warning manager 360 is used to determine what type of feedback to provide to the user in response to the detection and identification of a specific unsafe condition. In FIG. 4A, warning manager 360 is presented in a schematic view as including a plurality of safety response mechanisms 400 that can be triggered by the warning management system of FIG. 3 upon detection of a particular unsafe condition near the wearer. It may be appreciated that different embodiments could incorporate a different combinations of safety response mechanisms. Some embodiments, for example, could include only a single safety response mechanism.

In this case, warning manager safety systems 290 includes various safety response mechanisms applicable to drivers or other operators of vehicles, such as a forward-collision warning system, a blind-spot warning system, a rear cross-traffic warning system, and a lane departure warning system. These safety response mechanisms may help drivers to avoid dangerous situations such as potential collisions or a vehicle unintentionally departing from its lane or designated pathway. In addition, various safety response assistance mechanisms can be provided, such as a lane-keeping assist system and a lane-centering assist system. Furthermore, general safety response mechanisms applicable to both drivers and pedestrians can include an uneven surface warning, object avoidance warning, step(s) warning, slippery surface warning, and a more generic unsafe environment condition warning when the system recognizes a hazard but its classification has a degree of certainty below a given threshold. In addition, an alternate route recommendation module can be triggered in cases where the system determines that the path ahead should be completely avoided. It should be understood that these safety response mechanisms are presented for purposes of example only, and a wide variety of other mechanisms may be implemented as desired by the wearer. Each mechanism, when triggered, can provide a specific response or response sequence or pattern to the alert generator 370 of FIG. 3 that is adapted or specific to the type of unsafe condition that was identified, its proximity to the user, and/or the speed at which the unsafe condition is approaching.

In some embodiments, a user may also be able to select a particular profile type or operation mode for the system. In one embodiment, a user may choose one or more "roles" or modes offered by the system (e.g., via the application interface), and the selected mode can be employed by the warning management system when determining whether a condition is to be considered unsafe. The selected mode can also affect the type of alert or response that is presented to the user. As some non-limiting examples, some roles 450 that may be selected and linked to pre-configured profiles in the system include (a) pedestrian (walker); (b) cyclist; (c) jogger; (d) vision impaired (e.g., blind or legally blind); (e) hearing impaired (e.g., deaf or legally deaf); (f) dog walker (e.g. accompanying an animal); (g) motor-skill impairment (e.g., unable to walk without assistance, handicapped, wheelchair users, etc.); (h) pre-selected avoidance objects (e.g., allow the user to select specific objects that they wish to avoid); and (i) child or child caregiver (e.g., child or dependent is also relying on the system). It should be understood that these pre-configured profiles are presented for purposes of example only, and a wide variety of other profiles may be implemented as desired by the wearer and/or customized or custom-created by the wearer.

Figure 5A:
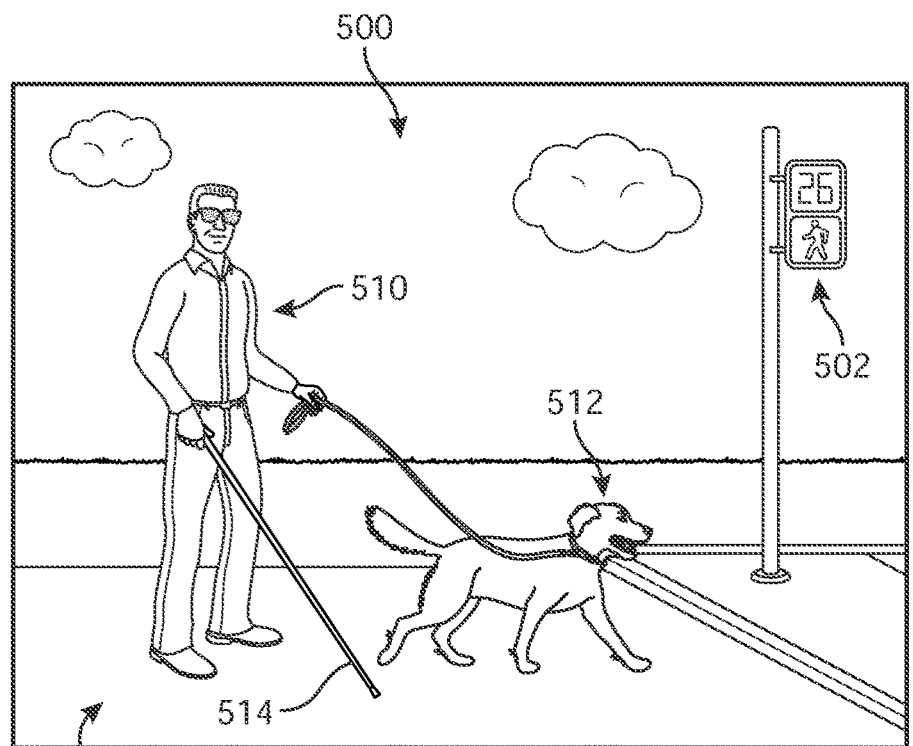
FIGS. 5A and 5B depict an example of a visually impaired person before and after employing a wearable environmental monitoring system, according to an embodiment.
Figure 5B:
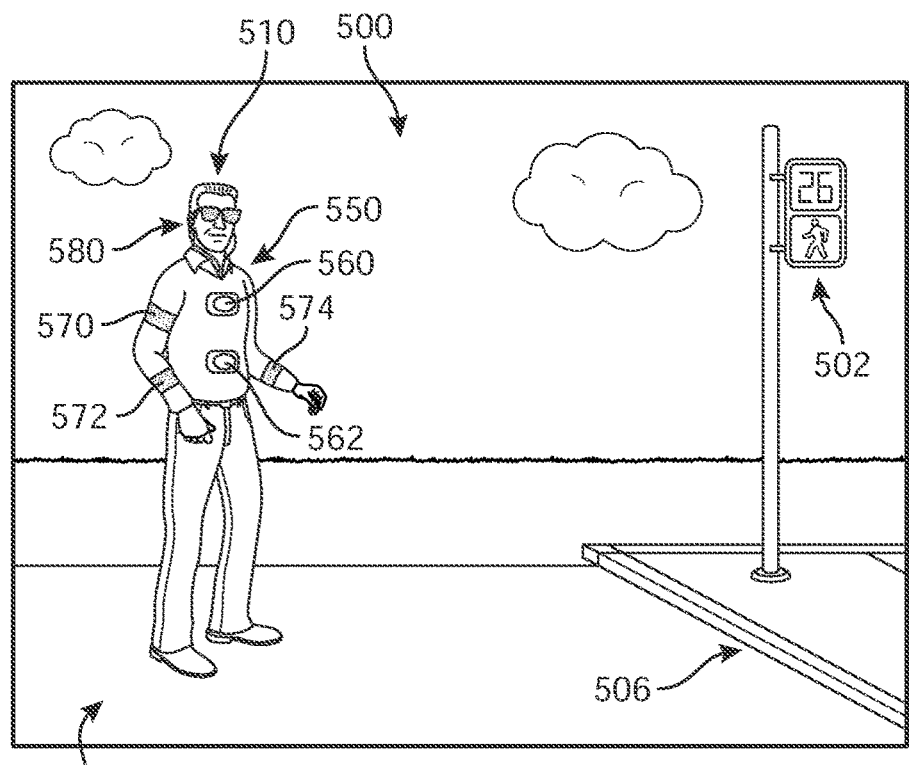

For purposes of illustration, some examples of the smart wearable system will be presented with reference to FIGS. 5A-5B, 6, 7, and 8. In FIGS. 5A and 5B, a visually impaired user 510 is shown walking on a crosswalk 504 in an urban area 500. In FIG. 5A, the visually impaired user 510 is walking with the assistance of a guide dog 512 and a probing cane 514. In this situation, the visually impaired user 510 must maintain care and attention to her animal, and is restricted in the use of her hands. In addition, while a guide dog is trained to navigate various obstacles, they are red-green color blind and incapable of interpreting street signals.

Thus, as one example, the green "GO" or walk indicator or a red "STOP" indicator on a traffic signal 502 is not information that can be used by the guide dog 512 or the visually impaired user 510.

In contrast, in FIG. 5B, the same visually impaired user 510 is walking along crosswalk 504 in urban area 500. However, in this case, the visually impaired user 510 is wearing a smart sweatshirt 550 that includes an embodiment of the systems described herein. For example, smart sweatshirt 550 includes a forward-facing sensor 562 disposed along her abdomen, and a first haptic-feedback component 560 disposed along her chest. In addition, a first arm sensor 572 can be seen on her right forearm and a second arm sensor 574 on her left forearm. A second-haptic feedback component 570 is located around her right upper arm. Other haptic-feedback components and sensors may also be arranged along various regions of the smart sweatshirt 550, such as around her neck, back, wrist, waist, shoulders, or other areas. The smart sweatshirt 550 also includes a controller system and rechargeable power source (see FIG. 2) that can be attached or integrated within the fabric of the wearable and connected to the sensors and feedback components (via a wired or wireless connection).

While wearing the smart sweatshirt 550, the visually impaired user 510 can be informed of upcoming obstacles and other unsafe conditions. Having selected the "vision impaired" mode (see FIG. 4B), the system is configured to alert the user to approaching the other side of the street (sidewalk 506) as well as the status of the traffic signal 502, and can convey this information to the visually impaired user 510, by audio signals emitted via headphones 560, and/or via tactile-based feedback. For example, in some embodiments, a series of audio messages can describe the distance to the end of the sidewalk, the difference in height between the sidewalk and road, whether a ramp or sloped surface is available, whether other pedestrians are ahead or nearby, whether vehicles are traveling on the roadway, as well as the current indicator being displayed by the traffic signal 502. Similarly, haptic-feedback components can be configured to vibrate on her left arm to either guide the user toward the left or alert the user to avoid the left, and to vibrate on her right arm to either guide the user toward the right or to avoid the right. The intensity of the vibration can correspond to the proximity of the impending obstacle. The vibration can also be emitted in a particular pattern that conveys to the visually impaired user 510 what type of obstacle is ahead. Vibrations can also serve as an alert to the user to stop, or to inform her that the conditions are now safe, or any other range of signals that can be established by either or both of the user and the system. For example, different patterns and intensities of vibrations along her abdomen can be triggered to suggest a slower or faster walking speed, or that the user is approaching a stairwell, the current status of a traffic signal ahead, a change in ground surface type or a narrowing of a path, the ending of a paved surface, or a slippery surface.

Figure 6:
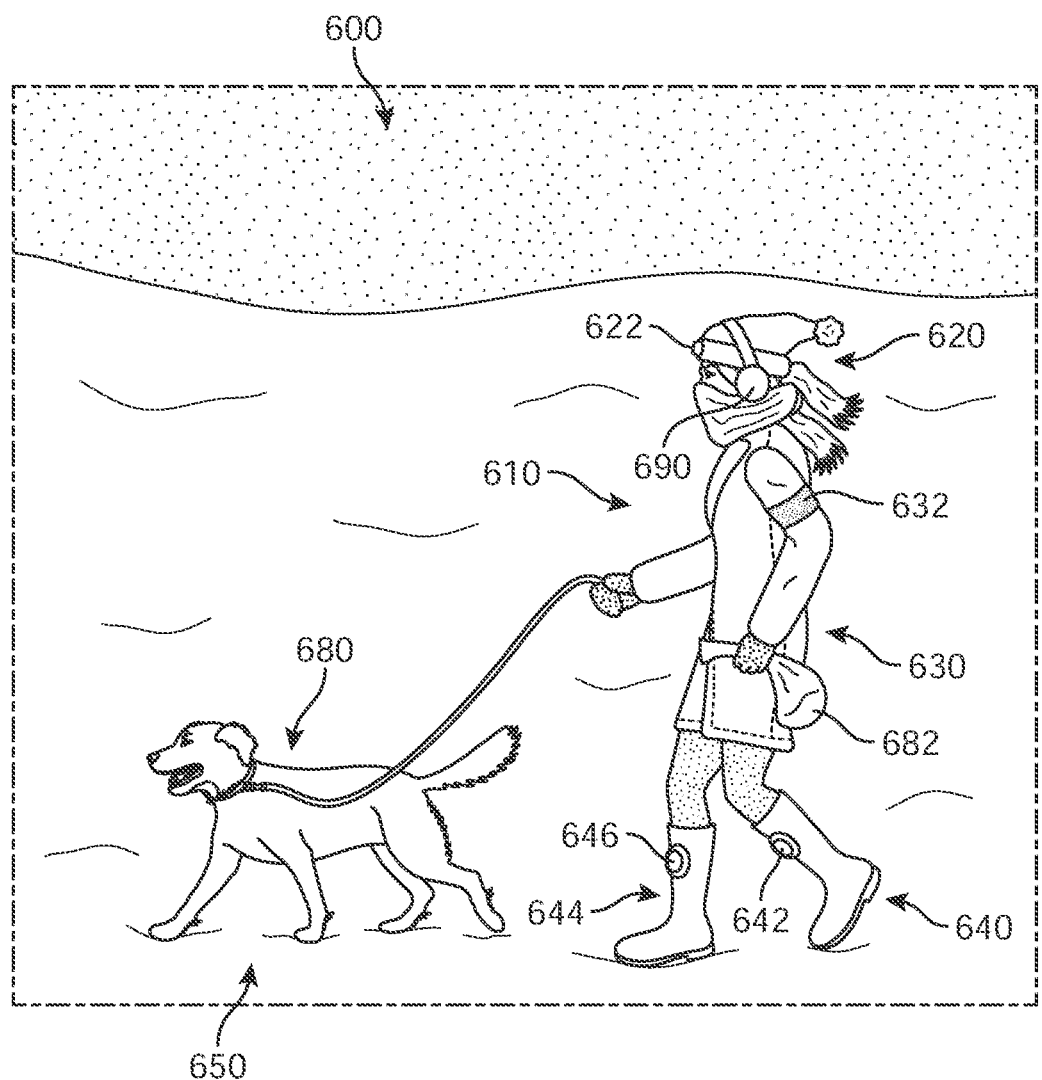
FIG. 6 is an illustration of a dog walker employing a wearable environmental monitoring system during low visibility conditions, according to an embodiment.

Other embodiments of the wearable environmental monitoring and alert system may include provisions for interconnecting multiple wearable articles to a single system. In FIG. 6, a dog walker 610 is trudging through snowy, windy, winter (low-visibility) conditions in a park 600 with her dog 680 held on a leash in one hand and a pet waste container 682 in her other hand. In addition, dog walker 610 is wrapped in several layers of clothing, including a scarf around her face, a beanie hat 620, a coat 630, and a pair of boots, including a first boot 640 and a second boot 644. In some embodiments, the system is configured to incorporate information from multiple smart articles and provide feedback through the same or other articles. In this case, simply for purposes of example, the beanie hat 620 can be seen to include a first sensor 622, while first boot 640 includes a second sensor 642 and second boot includes a third sensor 646.

In different embodiments, each of these sensors—and other sensors that may be disposed on other portions of her apparel, including the coat 630, scarf, leggings, gloves, etc.—can be part of a larger collection of wearables through which system 650 collects data. In other words, the multiple components of apparel, each with its own sensor assembly, can work in concert to provide a mesh sensor network, such as but not limited to networks employing Wireless Mesh Sensor Networks (WMSNs) technology and/or other distributed wireless sensor technology. The mesh sensor network can be used to connect separate sensor components, to connect sensor nodes with a cloud or remote monitoring platform, or provide a scalable backbone for sensor to sensor communication. Each sensor source communicates wirelessly with the controller, allowing the system to easily determine whether any unsafe conditions are near to the wearer. In some cases, a user may select the desired articles of apparel individually and then connect the selected items to permit communication among the sensors in each article. Thus, the user can customize their own "sensor outfit" that can include two or more smart articles of apparel that may be worn on different parts of the body, as shown in FIG. 6. In one embodiment, these smart articles can be registered and linked to a single user account, and can then be configured to communicate with and be managed by the same controller assembly. The sensor outfit can be worn by the same user at the same time and each piece of apparel operates as part of larger warning system. Each article of apparel can offer its own sensor array or arrangement, which can also be selected by the user depending on the type of apparel desired and/or the type of sensor desired. A set of headphones 690 can also be connected to the system to receive and emit audible feedback as described earlier. In some embodiments, a display or LED panel may also be worn or held by the user that is configured to receive messages and other information from the system.

In FIG. 6, the various sensors are wirelessly connected to a controller embedded in coat 630; however, in other embodiments, the controller can be located elsewhere on the user. Similarly, a plurality of feedback components can be distributed on any of the user's apparel items and wirelessly connected to the controller. In this case, a haptic feedback component 632 is wrapped around an upper arm of the dog walker 610. In different embodiments, the user can obtain additional articles of apparel that include other sensors and/or feedback components; each additional article can be registered with her system and operable as part of a smart ensemble network that is customized by the user and configured to communicate wirelessly to perform the variety of functions as described herein.

Figure 7:
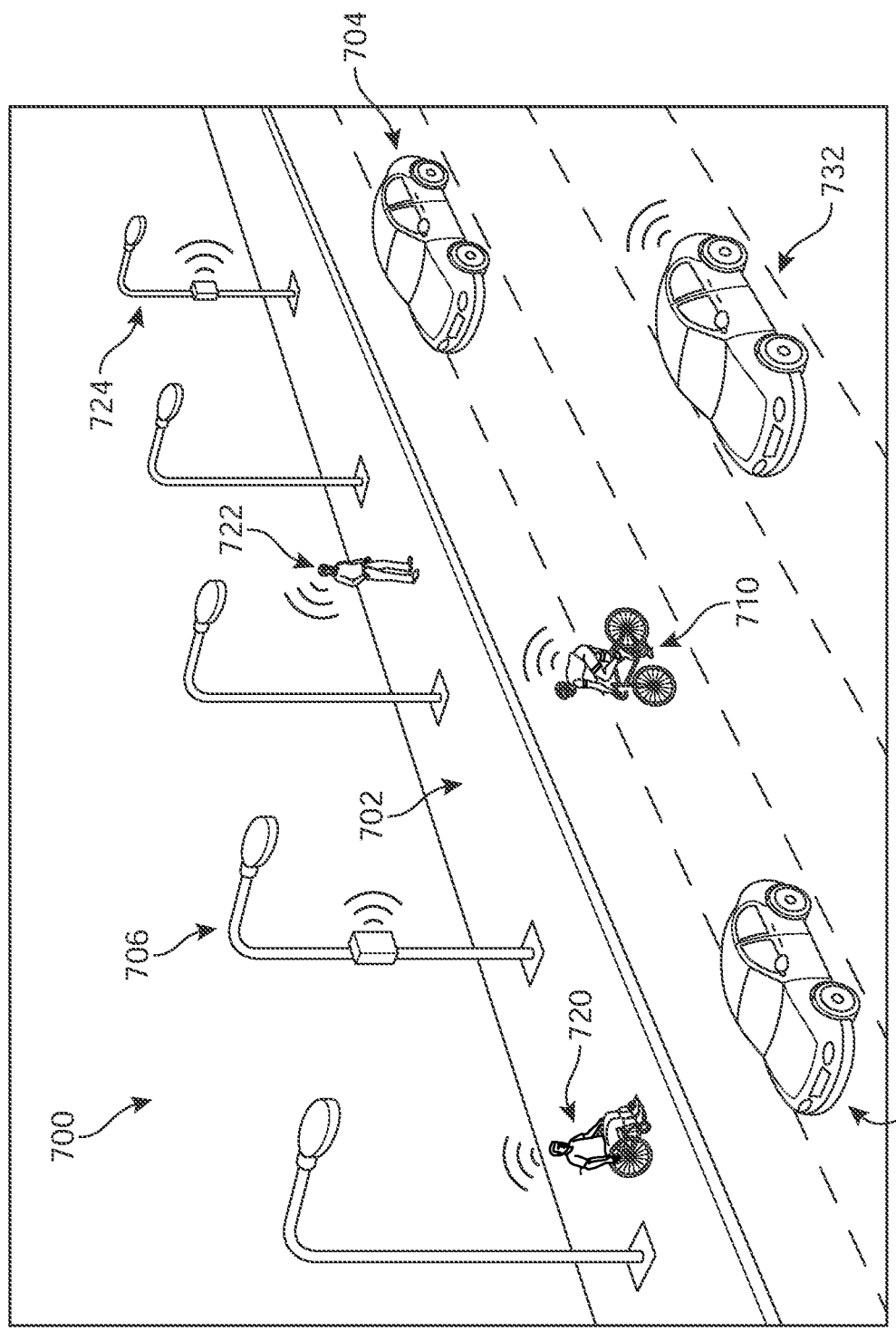
FIG. 7 is an illustration of an urban area in which multiple users are each employing wearable environmental monitoring systems, according to an embodiment.

In different embodiments, embodiments of the proposed system can include provisions for receiving data from sensors worn by the user as well as external databases and other on-site sensor sources (see FIG. 3). One example of such an arrangement is presented with respect to FIG. 7. In FIG. 7, an urban highway 700 is shown in which a plurality of sensors 724 are disposed along a roadway 704 at regular intervals. Specifically, a plurality of sensory assemblies is disposed on streetlights 706. In one embodiment, a sensory assembly can include one or more cameras, motion sensors, and wireless network devices configured to communicate over a network. The cameras may take images of roadway 704 as well as any passing vehicles. Such cameras could take still images or video. Image information captured by cameras could be analyzed to detect problematic driving behaviors (such as swerving, speeding or reckless driving). In some embodiments, image information captured by cameras could also be analyzed to detect vehicle collisions, unexpected obstacles, road work, or other aberrations in traffic that could represent a hazard to drivers. Motion sensors may also capture motion along, or near, roadway 704. In some cases, motion information detected by motion sensors could be used to trigger one or more other sensors, such as cameras. This allows other sensors to remain inactive until motion is detected. In some cases, information from motion sensors could also be used to detect stationary vehicles, either directly or indirectly. For example, if a motion sensor detects that a vehicle is not moving in the middle of a roadway, this information can be used to infer that the vehicle has either broken down or been involved in a collision. One or more of these on-site sensors may transmit data to a central database, allowing the data to be pooled and shared with wearable environmental monitoring and alert systems in the area, further expanding the capacity of that system to detect unsafe conditions in the area and provide alerts.

Figure 8:
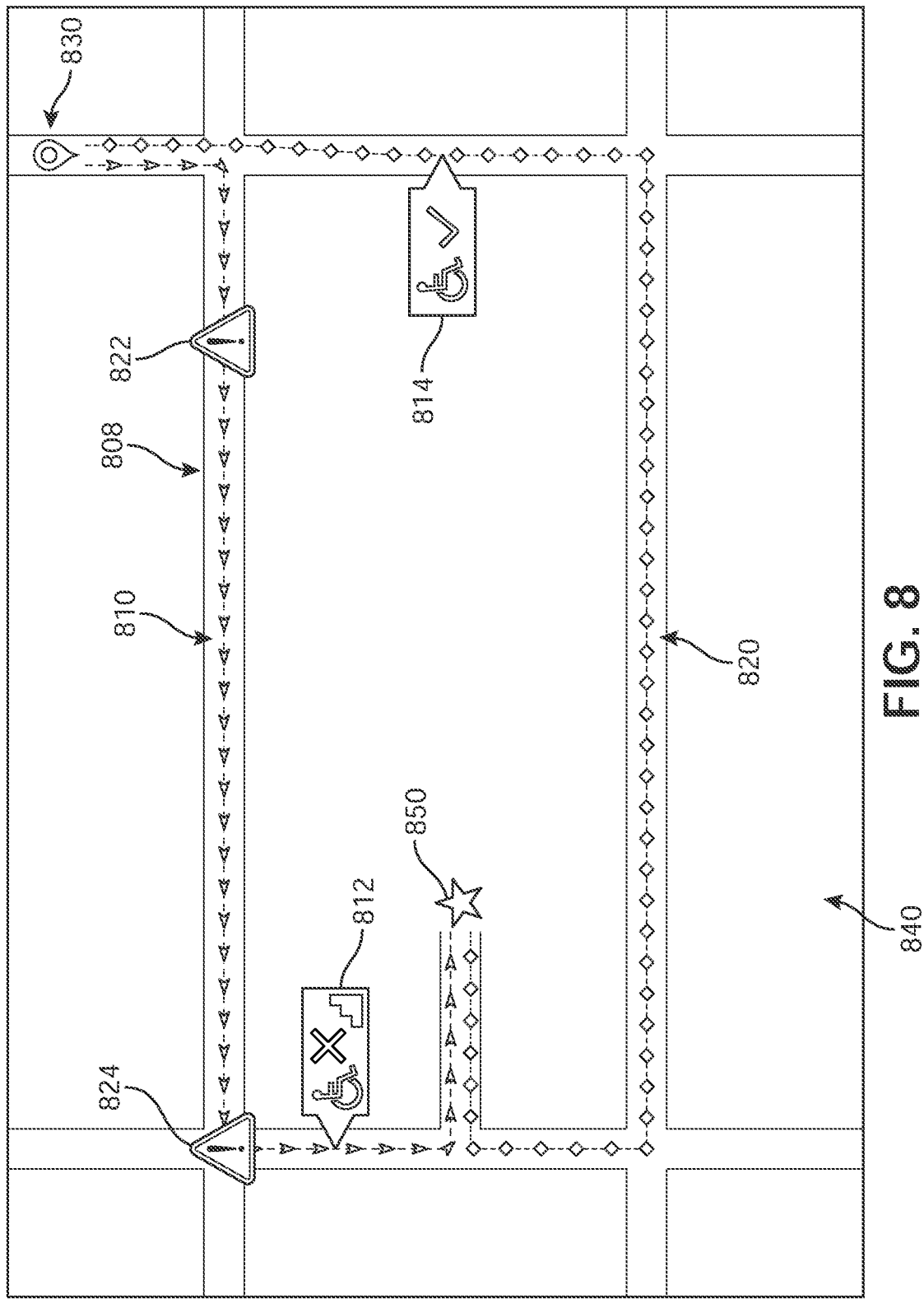
FIG. 8 is an example of a user interface for a wearable environmental monitoring system in which a new route is recommended to a disabled user, according to an embodiment.

In addition, systems worn by other users in the area can be configured to share data with a user device network (see FIG. 3). For example, a first user 720 in a wheelchair is moving along a sidewalk 702 adjacent to the roadway 704 while employing a first personal wearable environmental monitoring and alert system. Similarly, a second user 722 is also walking in the opposite direction (i.e., toward the first user 720) while employing a second personal wearable environmental monitoring and alert system. In some embodiments, one or more drivers on roadway 704 can also be using their own wearable environmental monitoring and alert system. For example, of a plurality of vehicles 730, a first vehicle 732 includes a driver or occupant who is currently employing a third personal wearable environmental monitoring and alert system. In addition, a biker 710 riding along the roadway 704 among vehicles 730 is employing a fourth personal wearable environmental monitoring and alert system. One or more of the wearable environmental monitoring and alert systems illustrated in FIG. 7 may be transmitting data from associated sensors being worn by their respective user to a central database, allowing the data to be pooled and shared with nearby systems, further expanding and enhancing the capacity of each system to accurately detect unsafe conditions in the area and provide alerts. The individual wearable systems can be configured to communicate via a network and thus may include any devices capable of communicating over one or more wireless networks. These include wide area networks, local area networks and personal area networks. display As noted earlier, in some embodiments, the proposed system can include provisions for rerouting users in response to the detection of unsafe conditions. One example of this arrangement is illustrated with respect to FIG. 8. In FIG. 8, a map 840 is depicted that may be shown to a wearer of a personal wearable environmental monitoring and alert system via a display included with or connected to the user's system. The user in this case is traveling in a wheelchair, currently located at a first position 830. The user has indicated he will be traveling along his normal route 810 via a first road 808 to a destination 850. However, the system, in communication with various databases, on-site sensors, and the local user device network, determines that the selected path includes obstacles such as sidewalk construction, surface irregularities or closures that would cause the user difficulty or may be otherwise unsafe, here identified as a first hazard 822 and a second hazard 824. The normal route 810 has been identified as undesirable by a first label 812. Instead, the system recommends a secondary route 820, which may be slightly longer, but is clear of any obstructions, and is otherwise wheelchair friendly, as identified by a second label 814. Thus, rather than discover belatedly that the user's planned route is impassable, the system can take advantage of its expanded network of information sources to help guide the user along a safer path to the same destination. In other embodiments, a user may enter their planned route to a new destination and the system can be configured to provide feedback about the selected path, such as the quality of the terrain, how steep or hilly the path will be, the traffic conditions in the area, and other such undesirable conditions.

Figure 9:
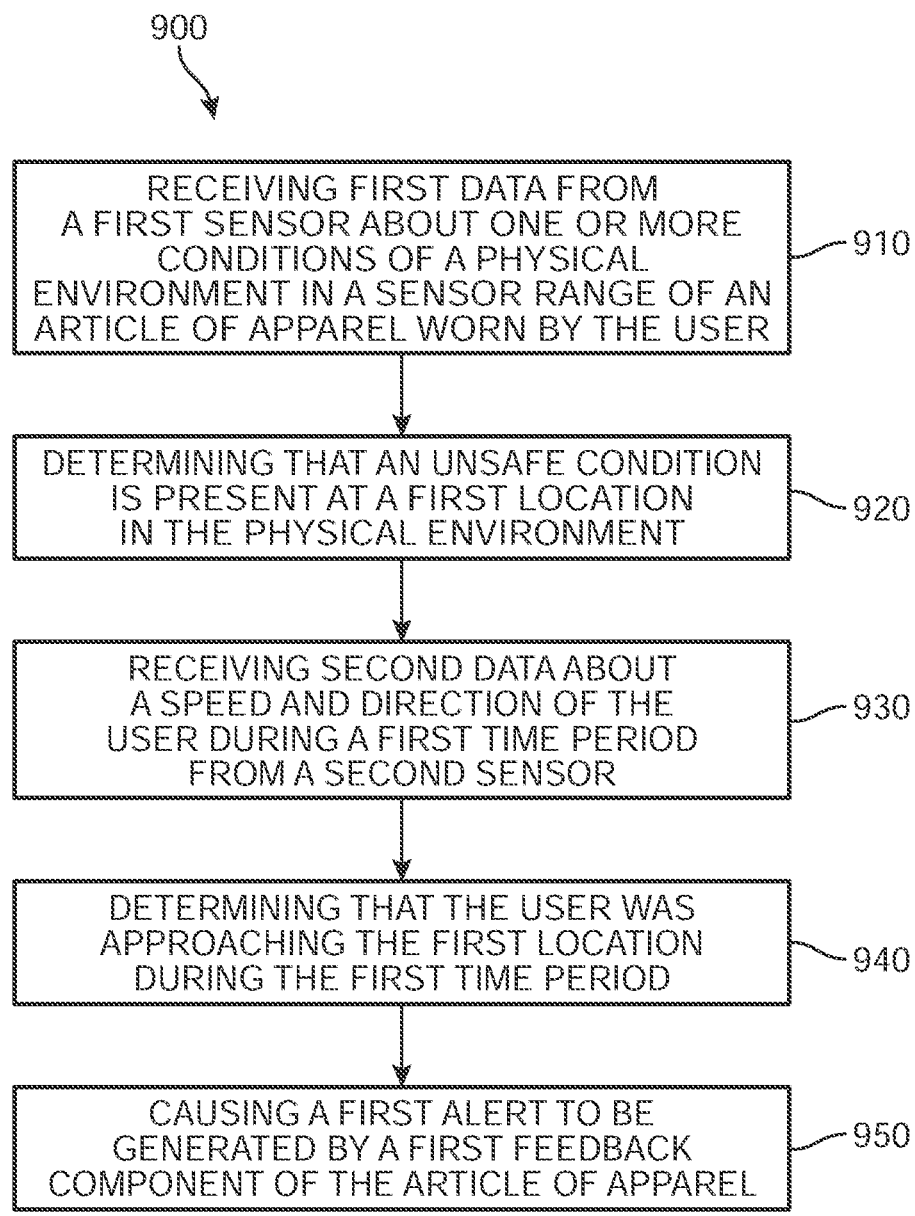
FIG. 9 is a flow chart depicting a process of alerting a user of a wearable environmental monitoring system of an approaching unsafe condition, according to an embodiment.

FIG. 9 is a flow chart illustrating an embodiment of a method 900 of alerting a user of a wearable environmental monitoring system to the presence of a nearby unsafe condition. A first step 910 includes receiving first data from a first sensor about one or more conditions of a physical environment in a sensor range of an article of apparel worn by the user. In this case, the article of apparel includes the first sensor. A second step 920 includes determining, based on the first data, that an unsafe condition is present at a first location in the physical environment, and a third step 930 includes receiving second data about a speed and direction of the user during a first time period from a second sensor of the article of apparel. In a fourth step 940 the method includes determining, based on the second data, that the user was approaching the first location during the first time period. Finally, a fifth step 950 includes causing, in response to the determination that the user is approaching the first location during the first time period, a first alert to be generated by a first feedback component of the article of apparel.

In other embodiments, the method may include additional steps or aspects. In one embodiment, the method can also include steps of receiving third data about a speed and direction of the user during a second time period subsequent to the first time period, determining, based on the second data, that the user continues to approach the first location during the second time period, and causing, in response to the determination that the user is approaching the first location during the second time period, a second alert to be generated by the first feedback component that is of a greater intensity than the first alert. In another example, the method can further include steps of causing, in response to the determination that the user is approaching the first location during the first time period, a second alert to also be generated by a second feedback component of the article of apparel. In this case, the first feedback component is configured to emit haptic feedback and the second feedback component is configured to emit audio feedback.

Furthermore, in some embodiments, the method also includes a step of receiving a selection of a first operation mode for the wearable environmental monitoring system, for example via a user interface for the system. In such cases, the determination that the unsafe condition is present at a first location in the physical environment is further based on the selected first operation mode.

In some embodiments, the first sensor is one of a camera, proximity sensor, and chemical sensor. In another example, the second sensor is one of a gyroscope, accelerometer, and motion sensor. In one embodiment, the first alert includes directions for avoiding the unsafe condition. In some cases, the first feedback component is configured to generate one of haptic-based output, audio-based output, and visual-based output.

In addition, in some embodiments, the system controller further comprises a communication module configured to receive and transmit data via a network connection. In another embodiment, the system controller is in communication with a first external database configured to provide current external weather conditions for a geographical area in which the article of apparel is located. In yet another example, the system controller is in communication with a first external database configured to provide current traffic and road conditions for a geographical area in which the article of apparel (and user) is located. In one embodiment, the system controller is in communication with a user device network configured to pool data received from other wearable environmental monitoring systems in order to more accurately detect unsafe conditions around each wearable environmental monitoring system. In some cases, the system controller is in communication with a wheelchair-accessible navigational database.

The embodiments discussed herein may make use of methods and systems in artificial intelligence to improve efficiency and effectiveness of the disclosed systems. As used herein, "artificial intelligence" may include any known methods in machine learning and related fields. As examples, artificial intelligence may include systems and methods used in deep learning and machine vision.

As described herein, the proposed systems and methods offer significant assistance and value to users, particularly those who are more vulnerable to safety issues in their environment. By including and employing multiple sensors and feedback components, the awareness of users of their surroundings can be enhanced and/or supplemented. As described herein, the wearable system could be used by people who are visually impaired or otherwise physically disabled. The wearable system can provide audible or proprioceptive feedback when safety issues are detected where a person is traveling. The audible or proprioceptive feedback could help guide a user around the safety issue. Additional information can be obtained in cases where multiple wearable systems are networked together in a user device network to share information about the current location of safety hazards. Furthermore, a hazard that may only be dangerous for someone walking may not be shared or result in an alert being presented to someone who is driving or riding a bike. This type of selective approach can ensure users are not distracted or inundated by unnecessary or irrelevant alerts.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with, or substituted for, any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

We claim:

1. A wearable environmental monitoring system comprising:
    an article of apparel including at least a first sensor and a second sensor, the article of apparel being one of a garment and footwear that is configured to be worn by a user;
    a system controller associated with the article of apparel, the system controller comprising a processor and machine-readable media including instructions which, when executed by the processor, cause the processor to:
        receive, from the user, a selection of a first operation mode that comprises a pre-configured profile which affects the type of alert that will be presented to the user;
        receive first data about one or more conditions of a physical environment in a sensor range of the article of apparel from the first sensor;
        determine, based on the first data and the selected first operation mode, that a first unsafe condition is present at a first location in the physical environment;
        receive second data about a speed and direction of the article of apparel during a first time period from the second sensor;
        determine, based on the second data, that the article of apparel was approaching the first location during the first time period;
        select a first alert type based on the first operation mode; and
        cause, in response to the determination that the article of apparel is approaching the first location during the first time period, a first alert of the first alert type to be generated by a first feedback component of the article of apparel.

2. The wearable environmental monitoring system of claim 1, wherein the instructions further cause the processor to:
receive third data about a speed and direction of the article of apparel during a second time period subsequent to the first time period;
determine, based on the second data, that the article of apparel continues to approach the first location during the second time period; and
cause, in response to the determination that the article of apparel is approaching the first location during the second time period, a second alert to be generated by the first feedback component that is of a greater intensity than the first alert, the first feedback component being a forward-facing haptic-feedback component providing tactile-based feedback and being disposed along the user's abdomen.

3. The wearable environmental monitoring system of claim 1, wherein the instructions further cause the processor to cause, in response to the determination that the article of apparel is approaching the first location during the first time period, a second alert to also be generated by a second feedback component of the article of apparel, wherein the first feedback component is disposed along a right arm of the user and the second feedback component is disposed along a left arm of the user.

4. The wearable environmental monitoring system of claim 3, wherein the first feedback component vibrates to alert the user to avoid the right and the second feedback component vibrates to alert the user to avoid the left.

5. The wearable environmental monitoring system of claim 1, wherein the second sensor is one of a gyroscope, accelerometer, and motion sensor.

6. The wearable environmental monitoring system of claim 3, wherein the first feedback component vibrates to guide the user toward the right and the second feedback component vibrates to guide the user toward the left.

7. A wearable environmental monitoring system for detecting unsafe conditions, comprising:
a first article of apparel being one of a vest, shirt, and sweatshirt that is configured to be worn by a user to which a first sensor and a first feedback component are attached;
a system controller associated with the first article of apparel and connected to both the first sensor and the first feedback component, the system controller being configured to:
receive, from the user, a selection of a first operation mode that comprises a pre-configured profile which affects the type of alert that will be presented to the user, and
select a first alert type based on the first operation mode; and
a rechargeable battery configured to provide power to the wearable environmental monitoring system.

8. The wearable environmental monitoring system of claim 7, wherein the first sensor is one of a camera, proximity sensor, chemical sensor, gyroscope, accelerometer, and motion sensor.

9. The wearable environmental monitoring system of claim 7, wherein the first feedback component is configured to generate one of haptic-based output, audio-based output, and visual-based output.

10. The wearable environmental monitoring system of claim 7, further comprising a second article of apparel being one of footwear and gloves to which a second sensor and a second feedback component are attached, and wherein the system controller is further connected to both the second sensor and the second feedback component.

11. The wearable environmental monitoring system of claim 7, wherein the system controller triggers the first feedback component to:
vibrate in a first pattern to alert the user when approaching a first type of hazard, and
vibrate in a second pattern to alert the user when approaching a second type of hazard that differs from the first type of hazard, the first pattern differing from the second pattern.

12. The wearable environmental monitoring system of claim 7, wherein the system controller triggers the first feedback component to vibrate in a first pattern to alert the user that they are approaching a slippery surface.

13. The wearable environmental monitoring system of claim 7, wherein the system controller triggers the first feedback component to vibrate in a first pattern to indicate the current status of a traffic signal ahead of the user.

14. The wearable environmental monitoring system of claim 10, wherein the system controller is in communication with a wheelchair-accessible navigational database, and the system controller triggers the first feedback component to vibrate in a first pattern to indicate the ending of a paved surface ahead of the user, as determined based on information in the wheelchair-accessible navigation database.

15. A method of alerting a user of a wearable environmental monitoring system to the presence of a nearby unsafe condition, the method comprising:
receiving first data from a first sensor embedded in an article of apparel worn by a user about one or more conditions of a physical environment, the article of apparel being one of a garment or footwear;
receiving, from the user, a selection of a first operation mode that comprises a pre-configured profile which affects the type of alert that will be presented to the user;
determining, based on the first data and the selected first operation mode, that a first unsafe condition is present at a first location in the physical environment;
receiving second data about a speed and direction of the user during a first time period from a second sensor of the article of apparel;
determining, based on the second data, that the user was approaching the first location during the first time period;
select a first alert type based on the first operation mode; and
causing, in response to the determination that the user is approaching the first location during the first time period, a first alert of the first alert type to be generated by a first feedback component of the article of apparel.

16. The method of claim 15, further comprising:
receiving third data about a speed and direction of the user during a second time period subsequent to the first time period;
determining, based on the second data, that the user continues to approach the first location during the second time period; and
causing, in response to the determination that the user is approaching the first location during the second time period, a second alert to be generated by the first feedback component that is of a greater intensity than the first alert, the first feedback component being a forward-facing haptic-feedback component providing tactile-based feedback and being disposed along the user's abdomen.

17. The method of claim 15, further comprising causing, in response to the determination that the user is approaching the first location during the first time period, a second alert to also be generated by a second feedback component of the article of apparel, wherein the first feedback component is disposed along a right arm of the user and the second feedback component is disposed along a left arm of the user.

18. The method of claim 17, wherein the first feedback component vibrates to alert the user to avoid the right and the second feedback component vibrates to alert the user to avoid the left.

19. The method of claim 15, wherein the second sensor is one of a gyroscope, accelerometer, and motion sensor.

20. The method of claim 17, wherein the first feedback component vibrates to guide the user toward the right and the second feedback component vibrates to guide the user toward the left.

\* \* \* \* \*